(12) United States Patent
Prest (10) Patent No.: US 6,808,933 B1
(45) Date of Patent: Oct. 26, 2004

(54) METHODS OF ENHANCING CONFIDENCE IN ASSAYS FOR ANALYTES

(75) Inventor: Harry F. Prest, Santa Clara, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 198 days.

(21) Appl. No.: 09/692,245

(22) Filed: Oct. 19, 2000

(51) Int. Cl.[7] .............................................. G01N 30/06
(52) U.S. Cl. ..................... 436/161; 73/23.41; 73/61.55; 210/656; 436/173
(58) Field of Search ................................. 436/161, 173; 422/70, 89; 210/656, 662, 198.2; 73/23.41, 61.55

(56) References Cited

U.S. PATENT DOCUMENTS

| 4,138,577 A | * | 2/1979 | Bundy et al. .................. 560/55 |
| 4,224,031 A | * | 9/1980 | Mee et al. .................... 436/173 |
| 4,273,784 A | * | 6/1981 | Bollinger .................... 514/530 |
| 4,784,962 A | * | 11/1988 | Apffel, Jr. et al. |
| 4,990,458 A | | 2/1991 | Rosenfeld ................... 436/174 |
| 5,428,173 A | * | 6/1995 | Kanai et al. ................. 548/128 |
| 5,952,336 A | * | 9/1999 | Cook et al. .................. 514/290 |
| 6,534,294 B1 | * | 3/2003 | Lee et al. .................... 435/101 |

OTHER PUBLICATIONS

Al–Majed, et al., J. of Pharmaceutical and Biomedical Analysis, 23–281–289 (2000); "Use of Mixed Anhydrides for the Determination of Terfenadine in Dosage Forms and Spiked Human Plasma".

* cited by examiner

*Primary Examiner*—Jan M. Ludlow
(74) *Attorney, Agent, or Firm*—Timothy H. Joyce (57) ABSTRACT

Methods are disclosed for enhancing the confidence index in detecting the presence and/or amount of an analyte suspected of being in a sample. In the method, a combination of at least two predetermined derivatives of the analyte is subjected to chromatographic separation. Then, the retention times of the derivatives as a result of the chromatographic separation are determined. The retention times are related to the presence of the analyte in the sample. Detecting a response from each of the derivatives enhances confirmation that the compound detected is the analyte in question further. The number and intensities of the responses is related to the presence and/or amount of the analyte in the sample.

22 Claims, 2 Drawing Sheets

METHODS OF ENHANCING CONFIDENCE IN ASSAYS FOR ANALYTES

BACKGROUND OF THE INVENTION

1. Field of the Invention

This invention relates to the field of identification or analysis of compounds. More particularly, the invention relates to enhancing the confidence index in detecting the presence and/or amount of an analyte and to the derivatization of organic compounds carried out in conjunction with the analysis or determination of various organic compounds. The present invention is described hereinbelow with emphasis on the analysis of organic compounds that are drugs of abuse and on the use of chromatography with mass spectroscopy in the analysis.

The clinical diagnostic field has seen a broad expansion in recent years, both as to the variety of materials of interest that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting the presence of these materials in low concentrations, as well as the confidence in their detection, are enhanced by the relatively small sample sizes that can be utilized.

Over the last decade, testing for drugs of abuse has become commonplace. This testing is not only for the monitoring of criminal offenders and drug addicts, but employers also use it for the screening of workers. In general, samples of interest are first tested by less expensive means such as immunoassays and the like. Such immunoassays include those based on detection employing various labels such as enzymes, fluorescent compounds, radioactive materials and so forth. Once a sample has been identified as positive for the presence of an analyte, it is often necessary or required to perform a confirmation test, which may be an immunoassay that differs from that used in the initial testing. In the area of testing for drugs of abuse, a confirmatory test may involve much more sophisticated and expensive technology such as gas chromatography and mass spectrometry or combinations thereof.

In recent years, techniques have been developed for the analysis or determination of organic compounds present in extremely small quantities or at very low concentrations. For example, by combining chromatographic techniques such as gas chromatography with various detection means such as mass spectrometry, sensitivity in the detection of analytes is enhanced.

The use of mass spectrometry for the identification of compounds and determination of their molecular structure is well known in the art. In one form of a mass spectrometer, a sample gas is partially ionized by electron impact or other means in an ion source. For each compound in the sample, a set of fragment ions are typically formed, each one having a particular mass to charge ratio, which is usually referred to as "mass."

The ions are separated by electric, magnetic or combined fields (in a mass analyzer) into different species according to their respective masses. In the usual arrangement of the mass analyzer, ions of one mass at a time are transmitted to a suitable detector for measurement and/or recording. Usually, the mass analyzer controls are manipulated so that the mass to charge ratio values are repeatedly and continuously swept over a selected mass range. A plot or tabulation of ion current or intensity versus mass to charge ratio is referred to as a mass spectrum and is the basic data output from a mass spectrometer.

By combining the techniques of gas chromatography with electron capture detection or mass spectrometry operating in the negative ion chemical ionization (NCI) mode, organic chemicals present in solution at concentrations of micrograms per ml or less can be analyzed. Such techniques are extremely useful for the analysis of aqueous fluids obtained from living organisms, such as plasma, serum, urine, etc., from man and other animals and liquid media from microorganisms.

One characteristic of such highly sensitive techniques is that they require the presence of certain specific groups in the molecule, for example, chromophores, fluorophores or electrophores. For instance, electron capture detection requires the presence of an electrophore (a group capable of capturing electrons), e.g., a group containing halogen atoms covalently bound to carbon. Unfortunately, many organic compounds of interest for analysis, particularly those from biological fluids mentioned above, do not possess such groups and must be converted to suitable derivatives as a preliminary step. In some cases it is also necessary to convert unstable compounds to stable derivatives.

There is a general reservation in the minds of at least some of those skilled artisans in using NCI for confirmation of the presence of a certain organic compound when there is limited fragmentation. For example, in the area of analyses for drugs of abuse, the use of NCI for confirmation of a positive test result from another testing method such as, for example, immunoassays and the like has not been widely adopted. In the latter situation there is only a primary molecular anion as the most intense ion in NCI. Those skilled in the art have focused their efforts on obtaining a single peak by purifying components and have achieved high intensity of signal. However, although signals of high intensity have been achieved, there is not enough mass information to provide a level of comfort amongst those skilled in the art, particularly in the area of confirmation of positive results in testing for drugs of abuse.

2. Brief Description of Related Art

U.S. Pat. No. 4,224,031 (Mee, et al.) discusses the chemical ionization mass spectrometric analysis of physiologically active compounds.

U.S. Pat. No. 4,990,458 (Rosenfeld) discloses the derivatization of organic compounds during their analysis or determination.

Use of mixed anhydrides for the determination of terfenadine in dosage forms and spiked human plasma is disclosed by Al-Majed, et al., in *Journal of Pharmaceutical and Biomedical Analysis* (2000) 23:281–289.

SUMMARY OF THE INVENTION

One embodiment of the present invention is a method for enhancing the confidence in detecting the presence of an analyte in a sample suspected of containing the analyte. In the method, a combination of at least two predetermined derivatives of the analyte is subjected to chromatographic separation. The predetermined derivatives exhibit different retention times as a result of the chromatographic separation. Then, the retention times of the derivatives are determined. The retention times are related to the presence of the analyte in the sample. This is a two-dimensional approach that relates the retention times as indicated by the detector signal to the presence of the compound.

Another embodiment of the present invention is a method for detecting the presence and/or amount of an analyte in a sample suspected of containing the analyte. A combination comprising at least two predetermined derivatives of the analyte is subjected to chromatographic separation to separate the derivatives, which are subjected to ionization to form ions as they exit from the chromatograph. A response from each of the ions is detected. The retention times of the ions and the ratios of the intensities of the responses are determined. The retention times and the ratios are related to the presence and/or amount of the analyte in the sample.

Another embodiment of the present invention is a method for detecting the presence and/or amount of a drug in a sample suspected of containing the drug. The sample is combined with at least two predetermined derivatizing agents to form at least two derivatives of the analyte. The derivatives are subjected to gas chromatographic separation to separate the derivatives. The separated derivatives are subjected to chemical ionization to form ions of the derivatives. The ions are subjected to mass analysis and a response from each is detected. The retention times of the ions and the ratios of the intensities of the responses are determined and the retention times and the ratios are related to the presence and/or amount of the drug in the sample.

Another embodiment of the present invention is a method for detecting the presence and/or amount of a drug of abuse in a sample suspected of containing the drug of abuse. The sample is combined with at least two predetermined derivatizing agents and then subjected to conditions under which derivatives of the analyte are formed. The derivatives are subjected to gas chromatographic separation to separate the derivatives and the separated derivatives are subjected to negative ion chemical ionization to form negative ions of the derivatives. The ions are subjected to mass analysis and a response from the ions is detected. The retention times of the ions and the ratios of the intensities of the responses are determined. The retention times and the ratios are related to the presence and/or amount of the drug in the sample.

DETAILED DESCRIPTION OF THE INVENTION

The present invention permits effective enhancement of confidence in the detection of an analyte in a sample suspected of containing the analyte. The level of confidence relates to the likelihood that the compound identified as being present in a sample is in fact present. It is important to have confidence in the performance of chromatographic and mass analysis techniques that the peak observed does indeed correspond to that produced by the presence of the analyte in question. As discussed above, confirmation that the compound detected is indeed the analyte in question is important, particularly in the area of confirmation of the presence and/or amount of a drug of abuse analyte.

The analytes are the compounds or compositions to be detected, usually monoepitopic or polyepitopic. The analyte may be a molecule found directly in a sample such as biological tissue, including body fluids, from a host. The sample can be examined directly or may be pretreated to render the analyte more readily detectable. The biological tissue includes excised tissue from an organ or other body part of a host such as, for example, hair, skin, fingernails, toe nails and the like and from body fluids such as, for example, urine, blood, plasma, serum, saliva, semen, stool, sputum, cerebral spinal fluid, tears, mucus, and the like.

Monoepitopic analytes will generally be from about 100 to about 2,000 molecular weight, more usually, from about 125 to about 1,000 molecular weight. The monoepitopic analytes include drugs, e.g., drugs of abuse and pharmaceutical drugs, metabolites, pesticides, pollutants, and the like. Included among drugs of abuse are the alkaloids. Among the alkaloids are morphine alkaloids, which includes morphine, codeine, heroin, dextromethorphan, their derivatives and metabolites; cocaine alkaloids, which include cocaine and benzoylecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol. The next group of drugs of abuse is lactams having from 5 to 6 annular members, which include the barbituates, e.g., phenobarbital and secobarbital, diphenylhydantoin, primidone, ethosuximide, and their metabolites. The next group of drugs is aminoalkylbenzenes, with alkyl of from 2 to 3 carbon atoms, which includes the amphetamines; catecholamines, which includes ephedrine, L-dopa, epinephrine; narceine; papaverine; and metabolites of the above. The next group of drugs of abuse includes those derived from marijuana, which includes cannabinol and $\Delta^9$-tetrahydrocannabinol (THC). The next group of drugs is benzheterocyclics, which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives. The next group of drugs includes hormones such as thyroxine, cortisol, triiodothyronine, testosterone, estradiol, estrone, progestrone, polypeptides such as angiotensin, LHRH, and immunosuppresants such as cyclosporin, FK506, mycophenolic acid, and so forth. The next group of drugs includes the vitamins such as A, B, e.g. B12, C, D, E and K, folic acid, thiamine. The next group of drugs is prostaglandins, which differ by the degree and sites of hydroxylation and unsaturation. The next group of drugs is the tricyclic antidepressants, which include imipramine, dismethylimipramine, amitriptyline, nortriptyline, protriptyline, trimipramine, chlomipramine, doxepine, and desmethyldoxepin. The next group of drugs is the antineoplastics, which include methotrexate. The next group of drugs is antibiotics, which include penicillin, chloromycetin, actinomycetin, tetracycline, terramycin, the metabolites and derivatives. The next group of drugs is the nucleosides and nucleotides, which include ATP, NAD, FMN, adenosine, guanosine, thymidine, and cytidine with their appropriate sugar and phosphate substituents. The next group of drugs is aminoglycosides, such as gentamicin, kanamicin, tobramycin, and amikacin.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Among pesticides of interest are polyhalogenated phenols, phosphate esters, thiophosphates, carbamates, polyhalogenated sulfenamides, their metabolites and derivatives. Metabolites related to diseased states include spermine, galactose, phenylpyruvic acid, and porphyrin Type 1.

The polyepitopic analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyepitopic analytes to which the subject invention can be applied have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight. Polynucleotide analytes include m-RNA, r-RNA, t-RNA, DNA, DNA-RNA duplexes, etc.

A wide variety of proteins are analytes such as, for example, proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc. The term analyte also includes receptors that are polynucleotide binding agents, such as, for example, restriction enzymes, activators, repressors, nucleases, polymerases, histones, repair enzymes, chemotherapeutic agents, and the like.

In the present method a combination of at least two predetermined derivatives of the analyte are subjected to separation by chromatographic techniques. The predetermined derivatives are selected on the basis of their ability to yield different retention times in the chromatographic separation of the derivatives and/or in their ability to yield different and/or additional detector responses. In this way additional information may be obtained when compared to the analysis of the analyte itself or a single analyte derivative through either additional chromatographic or detector signal or both forms of information. In general, any derivatization scheme may be employed so long as the overall principle of the present invention, which is discussed more fully hereinbelow, is followed.

The level of confidence desired in the present method is one factor in determining the number of derivatives. Other factors include detector type and response, derivatization efficiency, and matrix interferences from the sample. Usually, the number of derivatives is at least two, more usually, at least three, and preferably, at least three if detector response is non-discriminating. There is no upper limit on the number of derivatives except that the maximum number of derivatives is determined from a practical viewpoint, i.e., limiting of the number of reagents necessary for conducting the method and the amount of analyte.

The derivatives are chosen based on the overall principle that retention times for the derivatives and/or different and/or additional detector responses for the derivatives and their ratios enhance the confidence in detecting and confirming the presence of the analyte and the determined concentration of the analyte. In one aspect the derivatives are chosen to provide additional chromatographic information such as a separation in time of the derivatives produced by the chromatographic technique employed. In other words, multiple derivatives of a single analyte can produce additional retention time information indicating the presence of the analyte with enhanced confidence. Accordingly, the predetermined derivatives are chosen to provide predetermined retention times. Of course, the difference in retention times is dependent on the type of chromatographic technique performed and the chromatographic medium employed. In general, the derivatives are chosen so that the difference in retention times in the particular chromatographic technique performed is at least able to provide some minimal degree of resolution considered satisfactory by the analyst relative to the possible interferences or practical limitations such as analysis time, etc. Usually, it is desirable to achieve at least about 50% resolution and, preferably, greater than 70% resolution.

Furthermore, derivatives are chosen to, and usually inherently provide, different detector responses and/or additional detector responses. Different detector responses may result from the additional mass fragmentation patterns (mass spectrometry), the additional chromophore, or fluorophor, etc., available due to the additional derivative structure or composition. Additional detector responses may result from any absorbance or emission processes independent of the chromatographic processes of separation. As such, the differing responses generated by the derivatives mitigate the need for chromatographic separation.

Accordingly, the number and type of derivatives produced depends on the nature of the analyte and the nature of the chromatographic separation utilized. In general, chromatographic techniques involve the separation of compounds in a mixture by differences in the way the compounds become distributed (partitioned) between two phases. Chromatography may be gas chromatography, liquid chromatography, or combinations thereof, capillary electrophoresis, gel permeation or size exclusion chromatography, polyacrylamide gel electrophoresis, and the like. Separation methods for very small amounts of sample, e.g., a few milligrams or less, usually employ a combination of phases such as gas-liquid (vapor phase), liquid-solid, gas-solid (adsorbents) and the like.

More particularly, chromatography is based on the separation of different types of molecules as they pass along a chromatographic material usually confined in a housing such as a column. The housing may be packed with a material that provides a high surface area, e.g., packed column, or the material may be present as film coated on the walls of the internal walls of the housing, e.g., open tubular column. The packing or wall-coated film of inert material acts as a stationary phase. The chromatographic material is a material that exhibits attractive selectivity for certain compounds. The chromatographic material may interact physically with the compounds being analyzed. As a sample to be analyzed passes along the chromatographic material, it separates into its different components, which can then be characterized and identified. This approach can also be used to measure how much of each component is present in the mixture. Accordingly, the nature of the chromatographic material is one factor in selecting the nature and number of predetermined derivatives used in the present method.

One particular type of chromatography is gas chromatography, in which a sample is transformed into a gas phase. An inert gas is used as a carrier to propel the gaseous sample along the chromatographic material under constant conditions of mass flow rate. The inert gas passes along the chromatographic material at a constant velocity because it does not interact with, and therefore spend time on, the stationary phase. The sample is injected into the carrier gas and is swept along the chromatographic material. The different substances or analytes within the sample interact differently with the stationary phase, thus taking different times to pass through and exit the housing to reach a detector. This permits independent analysis of the analyte components.

Various approaches have been used to provide enhanced sensitivity in chromatographic separations. In one approach the diameter of the column has been decreased and its length has been increased. Very narrow columns (0.1 mm–0.5 mm internal diameter) are used. These are referred to as capillary columns and they may be several hundred feet long. These are not packed columns but, rather, the inside wall of the column is coated with a selective partitioning material. These capillary columns allow sample mixtures dissolved in 1 $\mu$l to 5 $\mu$l of solvent to be injected and analyzed.

Capillary zone electrophoresis is used for a wide variety of analyses including high resolution separations of various analytes. Capillary zone electrophoresis employs a capillary with an electric field gradient to separate the analyte constituents, particularly ions, by difference in electrophoretic mobilities in additional to electroosmotic flow in the capillary. The electroosmotic flow results when an electrical double layer of ions forms at the capillary surface and an electrical field is imposed lengthwise along the capillary. The field causes the ions to migrate toward the oppositely charged electrode at rates determined by the electrophoretic mobility of each analyte. In the resulting bulk electroosmotic flow, positively charged ions, neutral species, and negatively charged ions elute at different time intervals. The extent and speed of this separation are determined by differences in the electrophoretic mobilities of the analytes, the length of the capillary, the bulk electroosmotic flow and by the strength of electric field.

As mentioned briefly above, the formation of a single derivative of an organic compound as a step during its analysis as well as derivatizing reagents for forming such a derivative are known. For example, where the analysis involves highly sensitive techniques, the presence of certain specific groups in the molecule such as, for example, chromophores, fluorophores or electrophores is required. Many organic compounds do not possess such groups and must be converted to a suitable derivative as a preliminary step of the analysis. In some cases it is also necessary to convert an unstable compound to a stable derivative.

In the present invention, however, two or more predetermined derivatives for each analyte, rather than a single derivative for each analyte, are used as discussed above thereby creating multiple peaks of lower intensity than any single derivatization alone. This approach runs counter to the general thinking in the art that purified components are necessary in order to obtain a single peak and high intensity thereby maximizing the possibility of achieving the detection and correct identification of the analyte.

Forming a derivative of an analyte usually involves a derivatizing reagent that comprises a moiety such as a functional group reactive with a moiety such as functional group in the analyte. Typically, these reactions involve an active functional group on one molecule with an activate functional group on another. The derivatizing agent usually has a molecular weight of about 1 (addition of hydrogen) to about kilodaltons for DNA-adducts, more usually, about 80 to about 500 for common drug analysis. Generally, the predominant atom is carbon (C) but may also be oxygen (O), nitrogen (N), sulfur (S), phosphorus (P), wherein the O, N, S, or P. Heteroatoms, if present, are bound to carbon or one or more of each other or to hydrogen or a metal atom to form a functional group, such as, for example, carboxyl groups (carboxylic acids), hydroxyl groups (alcohols), mercapto groups (thiols), carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes, nitrites, chelators, organometallics and so forth.

In addition to the active functional group, the derivatizing agent generally comprises about 1 (for methylation) to greater than 100 carbon atoms for polymeric derivatives, usually, about 1 to about 7 carbon atoms, about 1 to about $C_nX_{2n+2}$ heteroatoms (X), usually, about 1 to about 10 heteroatoms (beyond those required for the bonding process), such as, for example, oxygen, nitrogen, sulfur, halogen and phosphorus. The derivatizing agent may comprise alkyl, alkylidine, aryl, or aralkyl, any one of which may be substituted with one or more of the aforementioned functional groups.

In a preferred embodiment the derivatizing agents are selected from the group consisting of organic acids, organic acid anhydrides, amines, alcohols, esters, organometallic compounds and complexing agents.

One or more of the aforementioned functional groups may be present on the analyte that is to be derivatized. The functional group on the analyte is reactive with the functional group on the derivatizing agent. In one aspect, one of the functional groups, usually, the functional group on the derivatizing agent, may be activated. Activated functional groups include, by way of example and not limitation, cyanogen bromide, N-hydroxysuccinimide esters, carbonyl diimidazole, carbodiimides, azlactones, cyanuric chlorides, organic sulfonyl chlorides, divinyl sulphone, nitrophenyl esters, iodoacetyl, maleimide, epoxy, hydrazide, reductive amination, diazonium salts, alkylating agents such as halo or tosylalkyl, oxy (hydroxyl or the sulfur analog, mercapto), active olefin such as a vinyl sulfone or α-, β-unsaturated ester and agents for Mannich condensations. Functional groups that react with the activated functional groups include, by way of example and not limitation, compounds containing active hydrogens, e.g., amines, alcohols, carboxylic acids, thiols, and carbonyls.

As an example, an amine-containing analyte can be attached to a carboxylic acid containing derivatizing agent by forming an activated ester of the carboxylic acid, such as an N-hydroxysuccinimide derivative. The amine readily reacts with this activated ester to form a stable amide bond. Activated functional groups may be linked to amine groups, carboxyl groups, nucleophiles (e.g. hydroxyl, thiol). Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed. Other examples are, by way of illustration and not limitation, reaction of an acid anhydride with an alcohol to form an ester, substitution (Sn1 and Sn2) such as with alkylating agents (or pentafluorbenzylbromide as used with halogenated phenols for example), condensation reactions, etc.

Preferred functional groups include, by way of illustration and not limitation, carboxylic acid (one to 8 carbon atoms) anhydrides where the carbon atoms are substituted with at least one chlorine or fluorine atom, preferably, substituted with chlorine or fluorine atoms equivalent to the number of potential hydrogen atoms, e.g., trifluroacetic acid anhydride, pentafluoropropionic acid anhydride, heptafluorobutyric acid anhydride, and so forth.

In forming the derivatives, the sample suspected of containing the analyte is combined with at least two predetermined derivatizing agents to form derivatives of the analyte. Usually, the sample is combined in a suitable medium with the derivatizing agents. The medium may be a protic solvent or an aprotic solvent. Usually, it is desirable to conduct reactions in a protic solvent because of the nature of the derivatizing agents and the analyte involved. The medium may be an aqueous medium that is solely water, a buffer, or that contains from about 0.01 to about 80 or more volume percent of a cosolvent such as an organic solvent. Such organic solvents include by way of illustration and not limitation oxygenated organic solvents of from 1 to about 6, more usually from 1 to about 4, carbon atoms, including alcohols such as methanol, ethanol, propanol, etc., ethers such as tetrahydrofuran, ethyl ether, propyl ether, etc., dimethylformamide, dimethylsulfoxide, and the like. Other co-solvents may be detergents including, by way of illustration and not limitation, Triton®, sodium dodecyl sulfate and the like. Usually these cosolvents, if used, are present in less than about 70 weight percent, more usually in less than about 30 weight percent.

Further discussion on the general aspects of derivatization of compounds may be found in Knapp, D. R. (1979) "Handbook of Analytical Derivatization Reactions," John Wiley and Sons, Inc.

The nature of the analyte and the nature of the derivatizing agent determine the pH for the medium. The pH for the medium will usually be in the range of about 2 to about 13, more usually in the range of about 3 to about 12, and for some analytes in the range of about 7 to about 11. The pH is generally selected to achieve optimum reaction between the molecules containing the reactive functional groups. Among the factors that must be considered is the pH dependence of the reactive molecules, concentration of reactive molecules and so forth. Various buffers may be used to achieve the desired pH and maintain the pH during the reaction. Illustrative buffers include acetate, borate, phosphate, carbonate, tris, citrate, barbital, various mixtures thereof and the like. The particular buffer or solvent employed is not critical to this invention, but in an individual reaction one or another buffer may be preferred.

The conditions employed are sufficient to permit the formation of products of the reaction of the analyte with the derivatizing agents. Moderate temperatures are preferably employed for carrying out reactions in accordance with the present invention, more preferably, room temperature. The temperature is usually in the range of from about 0° to about 100° C., more usually from about 50° to about 100° C. Higher or lower temperatures are employed where appropriate depending on the nature of the derivatizing agents, the analyte, other reagents employed in the reactions, the kinetics and so forth.

The predetermined amount of the derivatizing agents employed in the method of the present invention is dependent on a number of factors. In general, the amounts of the derivatizing agents are those necessary to achieve the result desired in accordance with the present invention. The amounts of derivatizing agents are usually based on the kinetics of the agents, the relative responses by the detection scheme(s) for the products, the estimated amount of analyte (stoichiometry) and so forth. In one aspect the predetermined amount of each derivatizing agent employed is not less than that which provides and equivalent signal for each derivative of the analyte thus providing the highest degree of confidence over the largest concentration range. The important feature is that each of the amounts of the derivatives formed is predetermined by the ratios of the agents and will be reflected in any internal standards that are used in the analysis and should be related those formed by the analyte itself. Accordingly, it should be understood that the yields of the derivatives formed under the conditions employed be taken into consideration in arriving at the predetermined amounts of the derivatizing agents employed and the predetermined amounts of the derivatives formed.

The time period for conducting the present method is dependent upon the specific reaction and reagents being utilized. Examples, by way of illustration and not limitation are: reaction of an amine-containing analyte with acid anhydrides or acid chlorides can require minutes; reaction of an amine-containing analyte with activated esters can require hours, ligand formation in solution can be seconds, and so forth.

As discussed above, in the next step of the present method, the derivatives are subjected to chromatographic separation to separate the derivatives. Then, the retention times of the derivatives as a result of the chromatographic separation are determined by various methods such as, for example, visual, spectrophotometric, thermal, electrical, mechanical, electromechanical, and the like to determine the retention times. Spectrophotometric techniques include, for example, mass spectrometric, absorption and emission spectrometric, such as fluorescence, and so forth. Thermal techniques include, for example, thermal conductivity, calorimetric, and so forth. Electrical techniques include, for example, solution conductivity, and so forth. Confirmation that the analyte is the analyte in question is then made based on the predicted or known retention times of the predetermined derivatives separated as discussed above and/or the presence of the distinguishing detector signals for the derivatives and their expected ratios. The appearance of each of the derivatives at the expected times indicates the presence of the analyte in the sample.

In addition to the retention times of the predetermined derivatives, a response from each of the derivatives and the respective intensities thereof may be detected. Detection of the intensities of the responses from the derivatives may be achieved by any convenient means including, for example, those mentioned above, namely, visual, spectrophotometric, thermal, electrical, mechanical, electromechanical, and the like.

Figure 1:
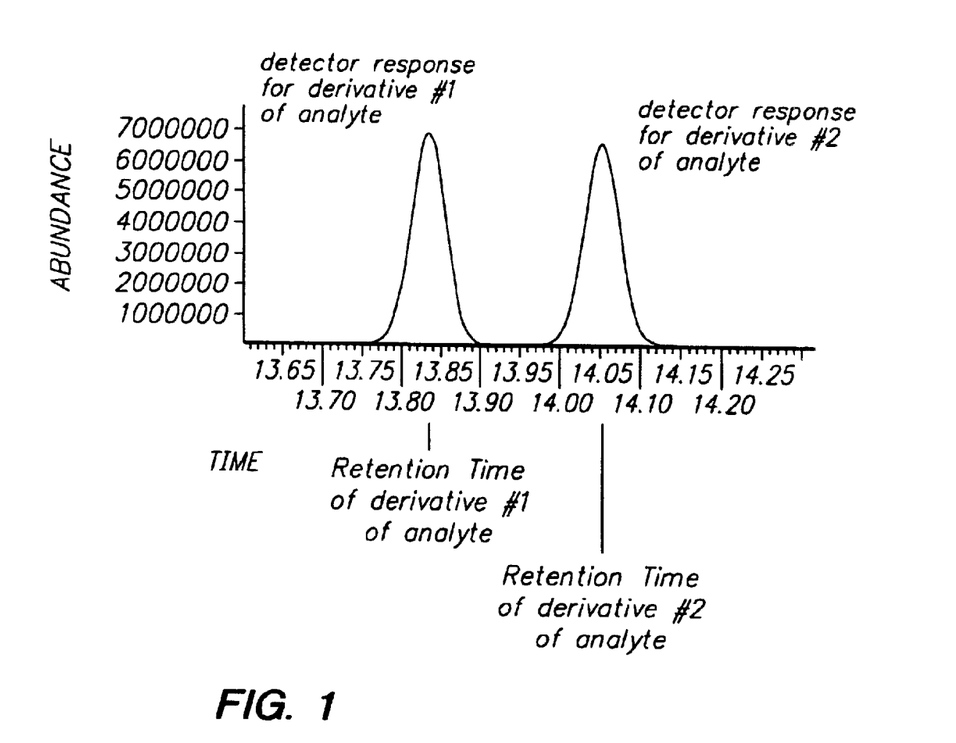
FIG. 1 is a schematic representation of two derivatives of a single analyte where chromatographic separation has been achieved in accordance with the present invention.

The number and intensities of the responses are related to the presence and/or amount of the analyte in the sample. Confirmation that the analyte is the analyte in question is then made based on the aforementioned predicted or known retention times of the predetermined derivatives, separated or not, as discussed above as well as the expected ratio of the intensities of the responses. The appearance of each of the derivatives at the expected times with the expected ratios indicates the presence of the analyte in the sample. For example, referring to FIG. 1, a schematic representation of two derivatives of a single analyte is depicted where chromatographic separation has been achieved. Both the signals at the expected retention times for the derivatives and the detector response ratio are indicative of the presence of the analyte.

One preferred method for detection is mass analysis such as mass spectrometry, which is an analytical methodology used for quantitative elemental analysis of materials and mixtures of materials. In mass spectrometric analysis, a sample is broken into charged particles. The charged particles are typically molecular fragments or adducts of molecules and intimately related to and indicative of the original substance. Once produced, the charged particles are separated by the spectrometer in relation to their respective masses or mass-to-charge ratios. The separated particles are then detected and a "mass spectrum" of the material is produced. The mass spectrum is analogous to a "fingerprint" of the sample material being analyzed. In particular, mass spectrometry provides information related to the structure and composition of the original unfragmented substance, which can be used to determine the molecular weights of molecules.

Figure 2A:
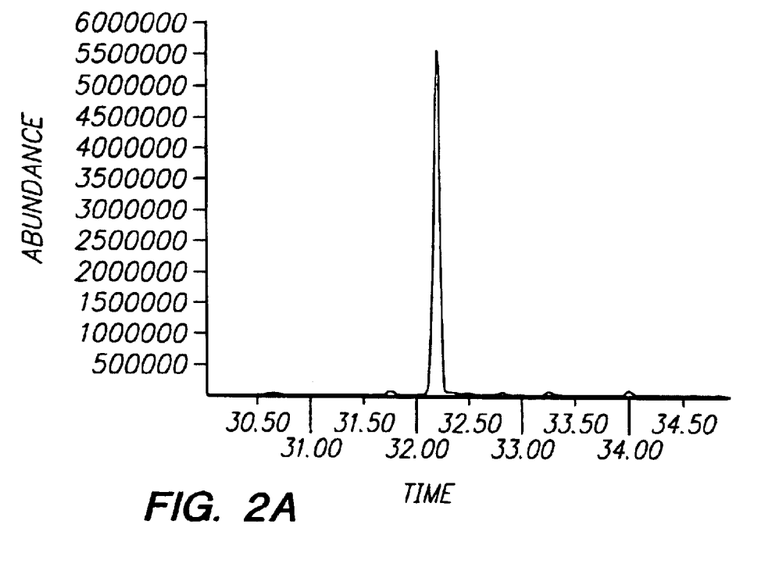
FIG. 2A is a schematic representation of two derivatives of a single analyte where a full chromatographic separation has not been achieved.
Figure 2B:
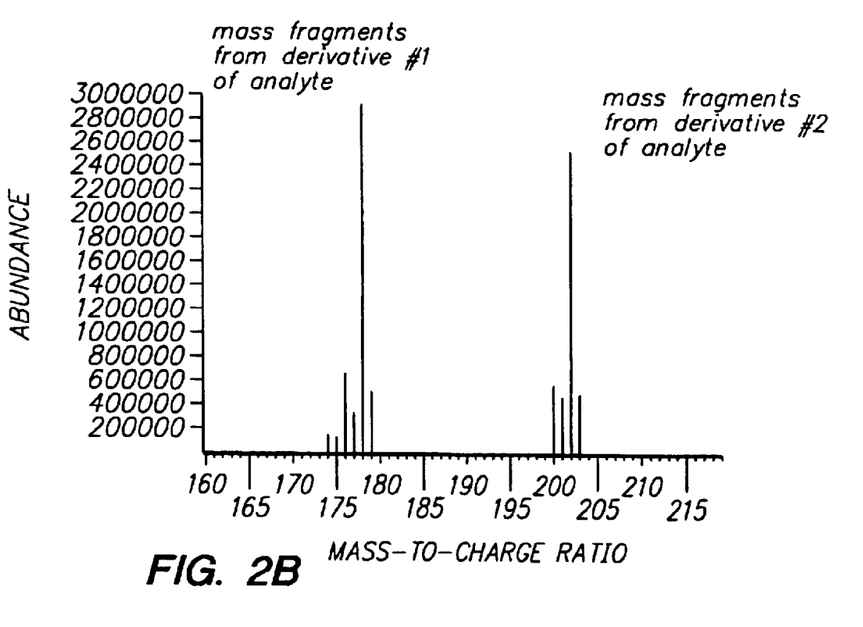
FIG. 2B is a schematic representation of the derivatives of FIG. 2A where the detector signal is capable of distinguishing the presence of the two derivatives by their signals in accordance with the present invention.

For example, referring to FIG. 2A, a graphic depiction of two derivatives of a single analyte is shown where a full chromatographic separation has been not been achieved. However, as seen in FIG. 2B, the detector signal is capable of distinguishing the presence of the two derivatives by their signals. In this example, the mass spectrometric fragments indicate the presence of both derivatives and therefore the analyte. It should be noted that both (i) the signals at the expected retention time for the derivatives and (ii) the ratio of the mass fragments are indicative of the presence of the analyte.

The methods of the present invention may be utilized in all mass spectrometry applications since mass spectrometry is simply one form of spectroscopy, specifically emission spectroscopy. The mass spectrometer may be, by way of example and not limitation, time-of-flight (TOF), ion trap, quadrupole, magnetic sector, Fourier-Transform (FT)-Ion Cyclotron Resonance (ICR), and the like. A general discussion of mass spectrometry may be found in McLafferty, F. W. and F. Turecek (1993) "Interpretation of Mass Spectra," University Science Books.

In a preferred embodiment of the present invention, the derivatives separated by chromatographic techniques are subjected to ionization to form ions of the derivatives, each having a particular mass to charge ratio. The ions are then subjected to mass analysis. The ionization may be, for example, chemical ionization, electrospray ionization, electron impact ionization, photoionization, electron capture ionization, fast ion or atom bombardment, field desorption, laser desorption, plasma desorption, thermospray, and inductively coupled plasma. The ions may be separated by electric fields or magnetic fields or a combination thereof in a mass analyzer into different species according to their respective masses. In one arrangement of a mass analyzer, ions of one mass at a time are transmitted to a suitable detector for measurement and/or recording.

An additional form of ionization is chemical ionization, which produces ions through a collision of molecules with primary ions present in the ionization chamber or by attachment of low energy electrons present in the chamber. A chemical ionization source operates at pressures that permit frequent collisions, typically, pressures from about 0.01 or lower to about 2 torr. This pressure may be attributed to the flow of a reagent gas, such as methane, isobutane, ammonia or the like, which is pumped into the chamber containing the chemical ionization source. In a typical configuration, both the reagent gas and the medium comprising each of the aforementioned separated derivatives of the analyte are introduced in to the chamber containing the chemical ionization source through gas-tight seals. The reagent gas and the derivatives are sprayed with electrons having energy of 1 eV to 300 eV from a filament through a small orifice, generally on the order of a few millimeters in diameter. Ions formed are extracted through a small orifice generally a few millimeters in diameter, and introduced into the analyzer or "filter" where they are characterized.

In the chemical ionization chamber of the chemical ionization source, the processes involving the analyte amounts to only a small fraction of the pressure attributable to the reagent gas. As a result, the electrons that are sprayed into the chamber predominately ionize the reagent gas molecules through electron impact. The resulting ions collide with other reagent gas molecules, frequently reacting to form other ions. These ions formed by reactions of the reagent gas, react with the analyte molecules via a numerous mechanisms including but not limited to proton transfer, additions, hydride abstractions, charge transfer and the like. The product ions formed can also undergo subsequent reactions such as dissociation. Negative ions can be formed by capture of slow (thermalized) electrons created in the source by analyte molecules or by other processes including those previously listed. A discussion of is chemical ionization may be found in Harrison, A. G. (1992) "Chemical Ionization Mass Spectrometry," CRC Press.

Another preferred ionization technique is electron impact ionization. An electron impact source generally contains a heated filament giving off electrons that are accelerated toward an anode and that collide with the gaseous analyte molecules introduced into the ionization chamber. Typically, the electrons have energy of about 70 eV and produce ions with an efficiency of less that a few percent. The total pressure within the ionization source is normally held at less than about $10^{-3}$ torr. The ions produced are extracted form the electron impact source with an applied electric field and generally do not collide with other molecules or surfaces form the time they are formed in the electron impact source until the time they are collected in the detector.

In a preferred embodiment of the invention, the separated derivatives of the analyte exiting from a chromatograph are subjected to electron capture or negative ion chemical ionization to form negative ions. Then, the negative ions of the analyte derivative may be separated according to their mass-to-charge ratio such as by subjecting the ions to a mass analyzer or filter.

Subsequently, the abundance of the ions of the analyte derivatives is measured usually by means of a detector, which is a device for recording ions that are subjected to manipulations in mass spectroscopy. The detector generally has high sensitivity and high dynamic range as well as providing good temporal resolution. When an analyte ion strikes the detector, the detector generates a signal. The time at which the signal is generated by the detector is used to determine the mass of the particle. In addition, for many detector types, the strength of the signal produced by the detector is proportional to the quantity of the ions striking it at a given point in time. Therefore, the quantity of particles of a given mass often can also be determined.

A number of different detector types are used in mass spectrometers. Among these are the channeltron, Daly detector, electron multiplier tube, Faraday cup and microchannel plate. Recently, hybrid electron multiplier detectors have been developed. Hybrid electron multiplier detectors have generally been based on the combination of a micro channel plate MCP multiplier and a discrete dynode multiplier, the classic multi-dynode electron multiplier (EM). Other detectors include, for example, surface ionization where reactions on a surface generate a signal, and the like.

Accordingly, in one embodiment of the invention, the separated derivatives are subjected to chemical ionization to form ions of the derivatives. The ions are subjected to mass analysis and a response from each is detected using an appropriate detector. A data processing system may be used to produce a mass spectrum of the analyte derivative. The retention times of the ions and the ratios of the intensities of the responses are determined and the retention times and the ratios are related to the presence and/or amount of the analyte in the sample. As discussed above, confirmation that the analyte is the analyte in question is then made based on the aforementioned predicted or known retention times of the predetermined derivatives separated as discussed above as well as the expected ratio of the intensities of the responses. The appearance of each of the derivatives at the expected times with the expected ratios indicates, and confirms, the presence of the analyte in the sample.

The present invention has particular application to mass spectrometry methods that are used in conjunction with a chromatographic technique. The combined analytic technique of gas chromatography and mass spectrometry is one such method wherein the gas chromatograph is directly interfaced with the mass spectrometer. Often, gas chromatography is employed specifically with quadrupole mass spectrometry. In another aspect the present invention has particular application in time-of-flight (TOF) mass spectrometry, which analyzes ions with respect to their ratio of mass and charge. The TOF mass spectrometer (TOFMS) uses the differences in the time of flight or transit time through the spectrometer to separate and identify the analyte constituent parts. TOFMS is used often in conjunction with liquid chromatography. Ion trap mass spectrometry is also used in conjunction with liquid chromatography and, thus, the present invention also has particular application to this form of mass analysis.

EXAMPLES

An example, by way of illustration and not limitation, of a method in accordance with the present invention is a confirmation assay for delta$^9$-tetrahydrocannabinol with the acid metabolite (THCA). The sample suspected of containing THC is combined in a suitable medium with two derivatizing agents, such as, trifluoroacetic anhydride (TFAA) and heptafluorobutyric anhydride (HFAA). The medium is treated under conditions for forming the derivatives of THC, namely, the derivatives produced by esterification of the hydroxy functionality of THC designated THC-TFA and THC-HFA, respectively. The medium is then subjected to gas chromatographic separation followed by analysis by negative chemical ionization mass spectrometry. Confirmation of the presence of THC in the sample is realized by the presence of the expected ions, corresponding to THC-TFA$^-$ and THC-HFA$^-$, at the expected ratio and retention times. The above experiment may also be carried out using the aforementioned derivatizing agents together with a third agent, namely, pentafluoropropionic anhydride (PFAA).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting the presence of an analyte in a sample, said method comprising:
    (a) combining said sample with at least two derivatizing agents to form a combination of at least two predetermined derivatives of said analyte:
    (b) subjecting said combination of at least two predetermined derivatives of said analyte to chromatographic separation;
    (c) determining the retention times and ratio of said derivatives as a result of said chromatographic separation; and
    (d) using said retention times and ratio to detect the presence of said analyte in said sample by comparison to expected retention times and an expected ratio.

2. A method according to claim 1 wherein said chromatographic separation is selected from the group consisting of gas chromatography, liquid chromatography, electrophoretic chromatography and combinations thereof.

3. A method according to claim 1 further comprising detecting a response from each of said derivatives and determining the intensities thereof, the number of intensities of said responses being related to the presence and/or amount of said analyte in said sample.

4. A method according to claim 3 wherein said detecting is conducted visually, spectrophotometrically, thermally, electrically, mechanically or electromechanically.

5. A method according to claim 1 wherein said analyte is selected from the group consisting of drugs of abuse, pharmaceutical drugs, metabolites, pesticides, pollutants, nucleotides, polynucleotides, polysaccharides, amino acids and poly(amino acids).

6. A method according to claim 1 wherein said derivatives are formed in situ.

7. A method for detecting the presence and/or amount of an analyte in a sample suspected of containing said analyte, said method comprising:

(a) combining said sample with at least two derivatizing agents to form a combination of at least two derivatives of said analyte;

(b) subjecting said combination of at least two predetermined derivatives of said analyte to chromatographic separation to separate said derivatives;

(c) subjecting said separated derivatives exiting from said chromatographic separation to ionization to form ions of said derivatives;

(c) detecting a response from each of said ions, and (d) determining the retention times of said ions and the ratios of the intensities of said responses; and (c) using said retention times and said ratios to detect the presence and/or amount of said analyte in said sample by comparison to expected retention times and an expected ratio.

8. A method according to claim 7 wherein said analyte is selected from the group consisting of drugs of abuse, pharmaceutical drugs, metabolites, pesticides, pollutants, nucleotides, polynucleotides, polysaccharides, amino acids and poly(amino acids).

9. A method according to claim 7 wherein said analyte is a drug of abuse.

10. A method according to claim 7 wherein said ionization is selected from the group consisting of chemical ionization, electrospray ionization, electron impact ionization, photoionization, and electron caption ionization.

11. A method according to claim 7 wherein said derivatives are formed in situ.

12. A method according to claim 7 wherein said detecting comprises subjecting said ions to mass analysis.

13. A method for detecting the presence and/or amount of a drug in a sample suspected of containing said drug, said method comprising:

(a) combining said sample with at least two predetermined derivatizing agents to from derivatives of said drug;

(b) subjecting said derivatives to gas chromatographic separation to separate said derivatives;

(c) subjecting said separated derivatives to chemical ionization to form ions thereof;

(d) subjecting said ions to mass analysis and detecting a response therefrom;

(e) determining the retention times of said ions and the ratios of the intensities of said responses; and (f) using said retention times and said ratios to determine the presence and/or amount of said drug in said sample by comparison to expected retention times and an expected ratio.

14. A method according to claim 13 wherein said chemical ionization comprises negative ion chemical ionization.

15. A method according to claim 13 wherein said drug is a drug of abuse.

16. A method according to claim 13 wherein said derivatizing agents are selected from the group consisting of organic acids, organic acid anhydrides, amines, alcohols, esters, organometallic compounds and complexing agents.

17. A method according to claim 13 wherein said derivatizing agents comprise at least one halogen moiety.

18. A method according to claim 13 wherein said drug of abuse is selected from the group consisting of alkoloids, steroids, lactams, aminoalkylbenzenes and benzyheterocycics.

19. A method for detecting the presence and/or amount of a drug of abuse in a sample suspected of containing said drug of abuse, said method comprising:

(a) combining said sample with at least two predetermined derivatizing agents, (b) subjecting said combination to conditions under which derivatives of said drugs are formed, (c) subjecting said derivatives to gas chromatographic separation to separate said derivatives, (d) subjecting said derivatives to negative ion chemical ionization to form negative ions of said derivatives, (e) subjecting said ions to mass analysis and detecting a response therefrom, (f) determining the retention times of said ions and the ratios of the intensities of said responses, and (g) using said retention times and said ratios to detect the presence and/or amount of said drug in said sample by comparison to expected retention times on an expected ratio.

20. A method according to claim 19 wherein said derivatizing agents are selected from the group consisting of organic acids, organic acid anhydrides, amines, alcohols, esters, organometallic compounds and complexing agents.

21. A method according to claim 19 wherein said derivatizing agents comprise at least one halogen moiety.

22. A method according to claim 19 wherein said drug of abuse is selected from the group consisting of alkaloids, steroids, lactams, aminoalkylbenzenes and benzheterocyclics.

* * * * *